(12) United States Patent
Howard et al.

(10) Patent No.: US 11,278,722 B2
(45) Date of Patent: Mar. 22, 2022

(54) SYSTEM AND METHOD TO CUE SPECIFIC MEMORY RECALLS WHILE AWAKE

(71) Applicant: HRL Laboratories, LLC, Malibu, CA (US)

(72) Inventors: Michael D. Howard, Westlake Village, CA (US); Praveen K. Pilly, West Hills, CA (US); Michael J. Daily, Thousand Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 296 days.

(21) Appl. No.: 16/374,433

(22) Filed: Apr. 3, 2019

(65) Prior Publication Data
US 2019/0224480 A1     Jul. 25, 2019

Related U.S. Application Data

(63) Continuation-in-part of application No. 15/990,460, filed on May 25, 2018, now Pat. No. 10,596,372, and
(Continued)

(51) Int. Cl.
*A61N 1/36*     (2006.01)
*A61N 1/04*     (2006.01)

(52) U.S. Cl.
CPC ....... *A61N 1/36025* (2013.01); *A61N 1/0456* (2013.01)

(58) Field of Classification Search
CPC .... A61N 1/36025; A61N 1/20; A61B 5/0476; A61B 5/4836; A61B 5/4812
See application file for complete search history.

(56) References Cited

U.S. PATENT DOCUMENTS 6,435,876 B1    8/2002   Chen
6,751,505 B1    6/2004   Van Den Honert
(Continued)

FOREIGN PATENT DOCUMENTS

CN     103079636 A     5/2013
CN     106512206 A     3/2017
(Continued)

OTHER PUBLICATIONS

Krause, B., & Cohen Kadosh, R. (2014). Not all brains are created equal: the relevance of individual differences in responsiveness to transcranial electrical stimulation. Frontiers in systems neuroscience, vol. 8, article 25, pp. 1-12.
(Continued)

*Primary Examiner* — Rex R Holmes
(74) *Attorney, Agent, or Firm* — Tope-McKay & Associates (57) ABSTRACT

Described is a system for cueing a specific memory in a waking state. The system sends an initiation signal to a memory recall controller to select a stored stimulation pattern previously associated with a specific memory of an event. The system signals to a memory recall controller to initiate delivery of the selected stimulation pattern to a brain in a waking state for a duration of the event via a brain stimulation system. Following completion of the event, the system signals for the memory recall controller to stop the brain stimulation system from delivering the selected stimulation pattern.

18 Claims, 6 Drawing Sheets

Related U.S. Application Data a continuation-in-part of application No. 15/947,733, filed on Apr. 6, 2018, now Pat. No. 10,413,724, which is a continuation-in-part of application No. 15/583,983, filed on May 1, 2017, now abandoned, and a continuation-in-part of application No. 15/332,787, filed on Oct. 24, 2016, now Pat. No. 10,307,592, which is a continuation-in-part of application No. 15/332,787, filed on Oct. 24, 2016, now Pat. No. 10,307,592, and a continuation-in-part of application No. 15/332,787, filed on Oct. 24, 2016, now Pat. No. 10,307,592, which is a continuation-in-part of application No. 15/227,922, filed on Aug. 3, 2016, now Pat. No. 10,092,753.

(60) Provisional application No. 62/681,503, filed on Jun. 6, 2018, provisional application No. 62/570,669, filed on Oct. 11, 2017, provisional application No. 62/558,133, filed on Sep. 13, 2017, provisional application No. 62/537,892, filed on Jul. 27, 2017, provisional application No. 62/516,350, filed on Jun. 7, 2017, provisional application No. 62/330,440, filed on May 2, 2016, provisional application No. 62/247,435, filed on Oct. 28, 2015, provisional application No. 62/245,730, filed on Oct. 23, 2015, provisional application No. 62/210,890, filed on Aug. 27, 2015, provisional application No. 62/210,907, filed on Aug. 27, 2015.

(56) References Cited

U.S. PATENT DOCUMENTS

| | | | |
|---|---|---|---|
| 7,153,139 B2 | 12/2006 | Wen et al. | |
| 8,718,778 B2 | 5/2014 | Bikson et al. | |
| 9,116,835 B1 | 8/2015 | Smyth | |
| 9,149,599 B2 | 10/2015 | Walter | |
| 9,370,658 B2 | 6/2016 | Neuvonen | |
| 2003/0225340 A1 | 12/2003 | Collura | |
| 2006/0041242 A1 | 2/2006 | Stypulkowski | |
| 2007/0060974 A1 | 3/2007 | Lozano | |
| 2007/0213786 A1 | 9/2007 | Sackellares et al. | |
| 2008/0045775 A1 | 2/2008 | Lozano | |
| 2008/0195166 A1 | 8/2008 | Sun | |
| 2009/0099623 A1 | 4/2009 | Bentwich | |
| 2009/0112278 A1 | 4/2009 | Wingeier | |
| 2009/0319002 A1 | 12/2009 | Simon | |
| 2011/0015469 A1 | 1/2011 | Walter | |
| 2011/0118534 A1 | 5/2011 | Baror | |
| 2011/0159467 A1 | 6/2011 | Peot | |
| 2011/0288610 A1 | 11/2011 | Brocke | |
| 2011/0313484 A1 | 12/2011 | Hincapie Ordonez et al. | |
| 2012/0046531 A1 | 2/2012 | Hua | |
| 2012/0184870 A1 | 7/2012 | Shaw | |
| 2012/0245653 A1 | 9/2012 | Bikson et al. | |
| 2012/0265261 A1 | 10/2012 | Bikson | |
| 2013/0011817 A1* | 1/2013 | Cohen Kadosh .. | A61N 1/36025 434/188 |
| 2013/0225953 A1 | 8/2013 | Oliviero | |
| 2013/0288223 A1 | 10/2013 | Watterson | |
| 2013/0338738 A1* | 12/2013 | Garcia Molina ...... | G09B 19/00 607/90 |
| 2014/0038147 A1 | 2/2014 | Morrow | |
| 2014/0057232 A1* | 2/2014 | Wetmore ............... | A61M 21/00 434/236 |
| 2014/0275926 A1 | 9/2014 | Scott et al. | |
| 2014/0288614 A1 | 9/2014 | Hagedorn | |
| 2015/0025590 A1 | 1/2015 | Cheng | |
| 2015/0050623 A1 | 2/2015 | Falash | |
| 2015/0066104 A1* | 3/2015 | Wingeier ........... | A61N 1/36025 607/45 |
| 2015/0079560 A1 | 3/2015 | Cowan | |
| 2015/0105837 A1 | 4/2015 | Aguilar Domingo | |
| 2015/0165206 A1 | 6/2015 | Venkatesan et al. | |
| 2015/0174418 A1 | 6/2015 | Tyler | |
| 2015/0238762 A1 | 8/2015 | Pal | |
| 2015/0294074 A1 | 10/2015 | Kawato | |
| 2016/0066838 A1 | 3/2016 | Decharms | |
| 2016/0175589 A1 | 6/2016 | Wingeier | |
| 2016/0206871 A1 | 7/2016 | Weisend | |
| 2016/0220850 A1 | 8/2016 | Tyler | |
| 2016/0228702 A1 | 8/2016 | Kempe | |
| 2016/0256691 A1 | 9/2016 | Cecchi | |
| 2016/0361541 A1 | 12/2016 | Wingeier et al. | |
| 2017/0014630 A1 | 1/2017 | Fried et al. | |
| 2017/0043167 A1 | 2/2017 | Widge | |
| 2017/0249853 A1 | 8/2017 | Weiss | |
| 2017/0304623 A1 | 10/2017 | Tandon | |
| 2017/0312519 A1 | 11/2017 | Pilly et al. | |
| 2018/0169411 A1 | 6/2018 | Goodall | |
| 2018/0221644 A1 | 8/2018 | Grill | |

FOREIGN PATENT DOCUMENTS

| | | |
|---|---|---|
| EP | 2409641 A1 | 1/2012 |
| JP | 2005-173081 A | 6/2005 |
| WO | WO2011159545 A2 | 12/2011 |
| WO | WO2016023126 A1 | 2/2016 |
| WO | WO2016/046830 A2 | 3/2016 |
| WO | WO2016046830 A2 | 3/2016 |
| WO | WO2016-102602 A1 | 6/2016 |
| WO | WO2016/145232 A2 | 9/2016 |
| WO | WO 2016-182947 A1 | 11/2016 |
| WO | WO2016205231 A1 | 12/2016 |
| WO | WO2017/075223 A1 | 5/2017 |

OTHER PUBLICATIONS

Santamecchi, E., Muller, T., Rossi, S., Sarkar, A., Polizzotto, N. R., Rossi, A., & Kadosh, R. C. (2016). Individual differences and specificity of prefrontal gamma frequency-tACS on fluid intelligence capabilities. Cortex, 75, pp. 33-43.

Bikson, M., Bestmann, S., & Edwards, D. (2013). Neuroscience: transcranial devices are not playthings. Nature, 501 (7466), p. 167.

Brunoni, A. R., Nitsche, M. A., Bolognini, N., Bikson, M., Wagner, T., Merabet, L., . . . & Ferrucci, R. (2012). Clinical research with transcranial direct current stimulation (tDCS): challenges and future directions. Brain stimulation, 5(3), pp. 175-195.

Schultz DM, Webster L, Kosek P, et al. (2012). Sensor-driven position-adaptive spinal cord stimulation for chronic pain. Pain Physician,15: pp. 1-12.

Philip P, Demotes-Mainard J, Bourgeois M, Vincent JD. (1991). Efficiency of transcranial electrostimulation on anxiety and insomnia symptoms during a washout period in depressed patients a double-blind study. Biol Psychiatry. Mar. 1;29(5): pp. 451-456.

Weiss MF. (1973). The treatment of insomnia through the use of electrosleep: an EEG study. J Nerv Ment Dis. Aug; 157(2): pp. 108-120.

Lande RG, Gragnani C. (2013) Efficacy of cranial electric stimulation for the treatment of insomnia: a randomized pilot study. Complement Ther Med.;21(1): pp. 8-13. doi: 10.1016/j.ctim.2012. 11.007.

Crenshaw MC, Edinger JD. (1999). Slow-Wave Sleep and Waking Cognitive Performance Among Older Adults With and Without Insomnia Complaints Physiology & Behavior, vol. 66, Issue 3, pp. 485-492.

Tyler WJ, Boasso AM, Mortimore HM, et al. (2015) Transdermal neuromodulation of noradrenergic activity suppresses psychophysiological and biochemical stress responses in humans. Scientific Reports;5:13865, pp. 1-17. doi:10.1038/srep13865.

Nitsche, M. A., Cohen, L. G., Wassermann, E. M., Priori, A., Lang, N., Antal, A., . . . & Pascual-Leone, A. (2008). Transcranial direct current stimulation: state of the art 2008. Brain stimulation, 1(3), pp. 206-223.

Ferrucci, R., Mameli, F., Guidi, I., Mrakic-Sposta, S., Vergari, M., Marceglia, S. E. E. A., . . . & Priori, A. (2008). Transcranial direct (56) References Cited

OTHER PUBLICATIONS current stimulation improves recognition memory in Alzheimer disease. Neurology, 71(7), pp. 493-498.
Clark, V. P., Coffman, B. A., Mayer, A. R., Weisend, M. P., Lane, T. D., Calhoun, V. D., . . . & Wassermann, E. M. (2012). TDCS guided using fMRI significantly accelerates learning to identify concealed objects. Neuroimage, 59(1), pp. 117-128.
Landolt, HP, Dijk, DJ, Achermann, P, Borbély, AA. (1996). Brain Research, 738(2): pp. 205-212.
Caffarel, J, Gibson, GJ, Harrison, JP, Giffiths, CJ, Drinnan, MJ. (2006). Comparison of manual sleep staging with automated neural network-based analysis in clinical practice. Med Biol Eng Comput., 44(1-2): p. 105-110.
Santostasi, G et al. (2016). Phase-locked loop for precisely timed acoustic stimulation during sleep. J Neurosci Methods, 259: pp. 101-114.
Nordin, M., Akerstedt, T. & Nordin, S. "Psychometric evaluation and normative data for the Karolinska Sleep Questionnaire," Sleep Biol. Rhythms, Oct. 2013, vol. 11, Issue 4, pp. 216-226.
Li, Z. et al. (2009). Unscented Kalman filter for brain-machine interfaces. Public Library of Science, 4(7): e6243, pp. 1-18.
Dmochowski JP, Datta A, Bikson M, Su Y, Parra LC. Optimized multi-electrode stimulation increases focality and intensity at target. J Neural Eng. 8(4):046011, pp. 1-16, 2011.
Weigenand, A., Mölle, M., Werner, F., Martinetz, T., & Marshall, L. (2016). Timing matters: open-loop stimulation does not improve overnight consolidation of word pairs in humans. European Journal of Neuroscience, 44(6), pp. 2357-2368.
Hoy, K. E., Emonson, M. R., Arnold, S. L., Thomson, R. H., Daskalakis, Z. J., & Fitzgerald, P. B. (2013). Testing the limits: investigating the effect of tDCS dose on working memory enhancement in healthy controls. Neuropsychologia, 51(9), p. 1777-1784.
Nader K, Schafe GE, Le Doux JE. Fear memories require protein synthesis in the amygdala for reconsolidation after retrieval. Nature. 2000; 406: pp. 722-726.
Dudai Y. The neurobiology of consolidations, or, how stable is the engram? Annu. Rev. Psychol. 2004; 55: pp. 51-86.
Squire LR, Alvarez P. Retrograde amnesia and memory consolidation: a neurobiological perspective. Curr. Opin. Neurobiol. 1995; 5: pp. 169-177.
Foa EB. Social anxiety disorder treatments: psychosocial therapies. J. Clin. Psychiatry. 2006; 67 Suppl 12: pp. 27-30.
Seidler GH, Wagner FE. Comparing the efficacy of EMDR and trauma-focused cognitive-behavioral therapy in the treatment of PTSD: a meta-analytic study. Psychol. Med. 2006; 36: pp. 1515-1522.
Bustos SG, Maldonado H, Molina VA. Midazolam disrupts fear memory reconsolidation. Neuroscience. 2006; 139: pp. 831-842.
Sandrini M, Censor N, Mishoe J, Cohen LG. Causal Role of Prefrontal Cortex in Strengthening of Episodic Memories through Reconsolidation. Curr. Biol. 2013; 23: pp. 2181-2184.
Soterix Medical Website. High Definition—transcranial Direct Current Stimulation (HD-tDCS) [Internet]. Available from: http://soterixmedical.com/hd-tdcs, downloaded Aug. 8, 2016, pp. 1-13.
Chan JCK, LaPaglia JA. Impairing existing declarative memory in humans by disrupting reconsolidation. Proc. Natl. Acad. Sci. 2013;110: pp. 9309-9313.
Brunet A, Orr SP, Tremblay J, Robertson K, Nader K, Pitman RK. Effect of post-retrieval propranolol on pychophysiologic responding during subsequent script-driven traumatic imagery in post-traumatic stress disorder. J. Psychiatr. Res. 2008;42: pp. 503-506.
Euston DR, Gruber AJ, McNaughton BL. The role of medial prefrontal cortex in memory and decision making. Neuron. 2012; 76: pp. 1057-1070.
Ji D, Wilson MA. Coordinated memory replay in the visual cortex and hippocampus during sleep. Nat. Neurosci. 2007; 10: pp. 100-107.
Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage. 2006; 30: pp. 813-826.
Dmochowski JP, Datta A, Bikson M, Su Y, Parra LC. Optimized multi-electrode stimulation increases focality and intensity at target. J. Neural Eng. 2011; 8:pp. 046011-1-046011-16.
Edmund Rolls, "The mechanisms for pattern completion and pattern separation in the hippocampus," Front Syst Neurosci. Oct. 2013; vol. 7: Article 74, pp. 1-21.
Thomas J. McHugh, et al., "Dentate Gyrus NMDA Receptors Mediate Rapid Pattern Separation in the Hippocampal Network," Science, vol. 317, (Jul. 2007); pp. 94-99.
Jesse Rissman, et al., "Distributed representations in memory: Insights from functional brain imaging," Annu Rev Psychol. 2012 ; 63: pp. 101-128.
Giulio Ruffinia, et al., "Optimization of multifocal transcranial current stimulation for weighted cortical pattern targeting from realistic modeling of electric fields," Neuroimage. Apr. 1, 2014; 89: pp. 216-225.
Office Action 1 for U.S. Appl. No. 15/072,353, dated Oct. 19, 2016.
Tremblay, Sara, et al., "The uncertain outcome of prefrontal TDCS," Brain Stimulation 7.6 (2014): pp. 773-783. Web.
Segrave, R.A., et al., "concurrent cognitive control training augments the anidepressant efficacy of TDCS: A pilot study," Brain Stimulation 7.2 (2014): pp. 325-331. Web.
Castano-Candamil, Sebastian, et al., "Solving the EEG inverse problem based on space-time-frequency structured sparsity constraints," Neuroimage 118 (2015), pp. 598-612. Web.
Response to Office Action 1 for U.S. Appl. No. 15/072,353, dated Feb. 17, 2017.
Office Action 2 for U.S. Appl. No. 15/072,353, dated Apr. 24, 2017.
"An automated pipeline for constructing personalized virtual brains from multimodal neuroimaging data," NeuroImage, vol. 117, Aug. 15, 2015, pp. 343-357.
Krause, M. R., Zanos, T. P., Csorba, B. A., Pilly, P. K., Choe, J., Phillips, M. E., Datta, A., and Pack, C. C. (2017). Transcranial direct current stimulation facilitates associative learning and alters functional connectivity in the primate brain. Current Biology, 27(3), pp. 3086-3096.
Response to Office Action 2 for U.S. Appl. No. 15/072,353, dated Aug. 22, 2017.
Office Action 3 for U.S. Appl. No. 15/072,353, dated Oct. 6, 2017.
Response to Office Action 3 for U.S. Appl. No. 15/072,353, dated Jan. 8, 2018.
Notice of Allowance for U.S. Appl. No. 15/072,353, dated Apr. 17, 2018.
Notification of the International Preliminary Report on Patentability Chapter I for PCT/US2019/025629; dated Oct. 15, 2020.
The International Preliminary Report on Patentability Chapter I for PCT/US2019/025629; dated Oct. 15, 2020.
Marshall L, Helgadóttir H, Mölle M, Born J. Boosting slow oscillations during sleep potentiates memory. Nature. 2006; 444(7119): pp. 610-613.
Rudoy JD, Voss JL, Westerberg CE, Paller KA. Strengthening Individual Memories by Reactivating Them During Sleep. Science. Nov. 20, 2009;326(5956): pp. 1079-1079.
Diekelmann S, Biggel S, Rasch B, Born J. Offline consolidation of memory varies with time in slow wave sleep and can be accelerated by cuing memory reactivations. Neurobiol Learn Mem. Sep. 2012; 98(2): pp. 103-111.
Rasch BH, Born J, Gais S. Combined blockade of cholinergic receptors shifts the brain from stimulus encoding to memory consolidation. J Cogn Neurosci. May 2006; 18(5): pp. 793-802.
Gais S, Bom J. Low acetylcholine during slow-wave sleep is critical for declarative memory consolidation. Proc Natl Acad Sci U S A. Feb. 17, 2004; 101(7): pp. 2140-2144.
Rasch B, Buchel C, Gais S, Born J. Odor cues during slow-wave sleep prompt declarative memory consolidation. Science. 2007; 315(5817): pp. 1426-1429.
Kirov R, Weiss C, Siebner HR, Born J, Marshall L. Slow oscillation electrical brain stimulation during waking promotes EEG theta activity and memory encoding. Proc. Natl. Acad. Sci. 2009;106: pp. 15460-15465.

(56) References Cited

OTHER PUBLICATIONS

Jutras MJ, Fries P, Buffalo EA. Oscillatory activity in the monkey hippocampus during visual exploration and memory formation. Proc Natl Acad Sci. Aug. 6, 2013; 110(32): pp. 13144-13149.
Brincat SL, Miller EK. Frequency-specific hippocampal-prefrontal interactions during associative learning. Nat Neurosci. Apr. 2015; 18(4): pp. 576-581.
McNamara CG, Tejero-Cantero A, Trouche S, Campo-Urriza N, Dupret D. Dopaminergic neurons promote hippocampal reactivation and spatial memory persistence. Nat Neurosci. 2014 12//print; 17(12): pp. 1658-1660.
Ji D, Wilson MA. Coordinated memory replay in the visual cortex and hippocampus during sleep. Nat Neurosci. 2007; 10(1): pp. 100-107.
Kali S, Dayan P. Off-line replay maintains declarative memories in a model of hippocampal-neocortical interactions. Nat Neurosci. 2004; 7(3): pp. 286-294.
Rolls ET. Hippocampo-cortical and cortico-cortical backprojections. Hippocampus. 2000; 10: pp. 380-388.
Creutzfeldt OD, Fromm GH, Kapp H. Influence of transcortical d-c currents on cortical neuronal activity. Exp Neurol. Jun. 1962; 5: pp. 436-452.
Sederberg PB, Kahana MJ, Howard MW, Donner EJ, Madsen JR. Theta and gamma oscillations during encoding predict subsequent recall. J Neurosci off J Soc Neurosci. Nov. 26, 2003; 23(34): pp. 10809-10814.
Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.
Fröhlich F, McCormick DA. Endogenous electric fields may guide neocortical network activity. Neuron. Jul. 15, 2010; 67(1): pp. 129-143.
Ngo, H. V. V., Martinetz, T., Born, J., & Molle, M. (2013). Auditory closed-loop stimulation of the sleep slow oscillation enhances memory. Neuron, 78(3), pp. 545-553.
Office Action 1 for U.S. Appl. No. 15/332,787, dated Sep. 18, 2018.
Response to Office Action 1 for U.S. Appl. No. 15/332,787, dated Nov. 6, 2018.
Notice of Allowance for U.S. Appl. No. 15/332,787, dated Jan. 17, 2019.
Merzagora, Anna C., G. Foffani, I. Panyavin, L. Mordillo-Mateos, J. Aguilar, Banu Onaral, and A. Oliviero. "Prefrontal hemodynamic changes produced by anodal direct current stimulation." Neuroimage 49, No. 3 (2010): pp. 2304-2310.
Christoff, J. A. (2002) Foreign Languages: Human Capital Approach Needed to Correct Staffing and Proficiency Shortfalls. Report to Congressional Requesters, pp. 1-50.
Operation and Maintenance Overview, Fiscal Year 2016 Budget Estimates, Feb. 2015, Office of the Under Secretary of Defense (Comptroller) / Chief Financial Officer, p. 13.
Flöel, A., Rosser, N., Michka, O., Knecht, S., & Breitenstein, C. (2008). Noninvasive brain stimulation improves language learning. Journal of Cognitive Neuroscience, 20(8), pp. 1415-1422.
Fregni, F., Boggio, P. S., Nitsche, M., Bermpohl, F., Antal, A., Feredoes, E., . . . & Pascual-Leone, A. (2005). Anodal transcranial direct current stimulation of prefrontal cortex enhances working memory. Experimental brain research, 166(1), pp. 23-30.
Acheson, D. J., Hamidi, M., Binder, J. R., & Postle, B. R. (2011). A common neural substrate for language production and verbal working memory. Journal of Cognitive Neuroscience, 23(6), pp. 1358-1367.
Anderson, J. R. (1981). Cognitive skills and their acquisition. Psychology Press, pp. 143-146 and pp. 243-249.
Bates, E., & MacWhinney, B. (1989). Functionalism and the competition model. The crosslinguistic study of sentence processing, 3, pp. 73-112.
Pienemann, M. (2005). An introduction to processability theory. Cross-linguistic aspects of processability theory, 30, pp. 179-199.
Schumann, J. H. (1986). Research on the acculturation model for second language acquisition. Journal of multilingual & multicultural development, 7(5), pp. 379-392.
Office Action 1 for U.S. Appl. No. 15/583,983, dated Feb. 12, 2019.
Apoorvagiri; Mental Stress and its Implications on Reaction time; International Journal of Computer Trends and Technology; May 2013; Mental Stress and its Imprilcations on Reaction time. (Year 2013).
Bikson, M., Bestmann, S., & Edwards, D. (2013). Neuroscience: transcranial devices are not playthings. Nature, 501 (7466), pp. 167-167.
Choe, J., Coffman, B. A., Bergstedt, D. T., Ziegler, M. D., & Phillips, M. E. (2016). Transcranial direct current stimulation modulates neuronal activity and learning in pilot training. Frontiers in human neuroscience, 10, pp. 1-25.
Schultz DM, Webster L, Kosek P, et al. Sensor-driven position-adaptive spinal cord stimulation for chronic pain. Pain Physician 2012;15: pp. 1-12.
Jacobson, L., Koslowsky, M., & Lavidor, M. (2012). tDCS polarity effects in motor and cognitive domains: a meta-analytical review. Experimental brain research, 216(1), pp. 1-10.
Osorio I, Frei MG, Sunderam S, et al. Automated seizure abatement in humans using electrical stimulation. Ann Neurol 2005;57: pp. 258-268.
Berényi, A., Belluscio, M., Mao, D., & Buzsáki, G. (2012). Closed-loop control of epilepsy by transcranial electrical stimulation. Science, 337(6095), pp. 735-737.
Tergau, F., Naumann, U., Paulus, W., & Steinhoff, B. J. (1999). Low-frequency repetitive transcranial magnetic stimulation improves intractable epilepsy. The Lancet, 353(9171), p. 2209.
Gálvez-García, G., Albayay, J., Rehbein, L., & Tomay, F. (2017). Mitigating Simulator Adaptation Syndrome by means of tactile stimulation. Applied Ergonomics, 58, pp. 13-17.
Ngo, H. V. V., Miedema, A., Faude, I., Martinetz, T., Mölle, M., & Born, J. (2015). Driving Sleep Slow Oscillations by Auditory Closed-Loop Stimulation—A Self-Limiting Process. The Journal of Neuroscience, 35(17), pp. 6630-6638.
Cox, R., Korjoukov, I., de Boer, M., & Talamini, L. M. (2014). Sound asleep: processing and retention of slow oscillation phase-targeted stimuli. PloS one, 9(7), e101567, pp. 1-12.
Santostasi, G., Malkani, R., Riedner, B., Bellesi, M., Tononi, G., Paller, K. A., & Zee, P. C. (2016). Phase-locked loop for precisely timed acoustic stimulation during sleep. Journal of neuroscience methods, 259, pp. 101-114.
Van Elmpt WJ, Nijsen TM, Griep PA, et al. A model of heart rate changes to detect seizures in severe epilepsy. Seizure 2006; 15: pp. 366-375.
Schade CM, Schultz DM, Tamayo N, et al. Automatic adaptation of neurostimulation therapy in response to changes in patient position: results of the Posture Responsive Spinal Cord Stimulation (PRS) Research Study. Pain Physician 2011;14: pp. 407-417.
Little S, Pogosyan A, Neal S, et al. Adaptive deep brain stimulation in advanced Parkinson disease. Ann Neurol 2013;74: pp. 449-457.
Notification of Transmittal of International Search Report and the Written Opinion of the International Searching Authority for PCT/US2018/026614; dated Aug. 27, 2018.
International Search Report of the International Searching Authority for PCT/US2018/026614; dated Aug. 27, 2018.
Written Opinion of the International Searching Authority for PCT/US2018/026614; dated Aug. 27, 2018.
Office Action 1 for U.S. Appl. No. 15/947,733, dated Feb. 1, 2019.
Response to Office Action 1 for U.S. Appl. No. 15/947,733, dated Apr. 16, 2019.
Notice of Allowance for U.S. Appl. No. 15/947,733, dated May 8, 2019.
Grech, R., Cassar, T., Muscat, J., Camilleri, K.P., Fabri, S.G., Zervakis, M., Xanthopoulos, P., Sakkalis, V. and Vanrumste, B., 2008. Review on solving the inverse problem in EEG source analysis. Journal of neuroengineering and rehabilitation, 5(1), pp. 1-33.
Tucker DM. Spatial sampling of head electrical fields: the geodesic sensor net. Electroencephalogr. Clin. Neurophysiol, 87: pp. 154-163, 1993.

(56) References Cited

OTHER PUBLICATIONS

Michel C., Murray MM. Towards the utilization of EEG as a brain imaging tool, NeuroImage 61 (2012), pp. 371-385.

Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage, 30: pp. 813-826, 2006.

Dmochowski JP, Datta A, Bikson M, Su Y, Parra LC. Optimized multi-electrode stimulation increases focality and intensity at target. J. Neural Eng., 8:046011, 2011, pp. 1-16.

Jones DK and Leemans A, "Diffusion Tensor Imaging", Methods in Molecular Biology 711: pp. 127-144, 2011.

Ramfrez, Rey R., and Scott Makeig. "Neuroelectromagnetic source imaging of spatiotemporal brain dynamical patterns using frequency-domain independent vector analysis (IVA) and geodesic sparse Bayesian learning (gSBL)." In Proceedings of the 13th Annual Meeting of the Organization for Human Brain Mapping, Chicago, IL. 2007.

Office Action 1 for U.S. Appl. No. 15/338,118, dated May 23, 2018.

Fox, Peter T., et al., "Column-based Model of Electric Field Excitation of Cerebral Cortex," Human Brain Mapping 22:1-16 (2004).

Response to Office Action 1 for U.S. Appl. No. 15/338,118, dated Aug. 23, 2018.

Office Action 2 for U.S. Appl. No. 15/338,118, dated Nov. 21, 2018.

Response to Office Action 2 for U.S. Appl. No. 15/338,118, dated Feb. 21, 2019.

Notice of Allowance for U.S. Appl. No. 15/338,118, dated Mar. 11, 2019.

Gais S, Born J. Low acetylcholine during slow-wave sleep is critical for declarative memory consolidation. Proc Natl Acad Sci U S A. Feb. 17, 2004; 101(7): pp. 2140-2144.

McNamara CG, Tejero-Cantero A, Trouche S, Campo-Urriza N, Dupret D. Dopaminergic neurons promote hippocampal reactivation and spatial memory persistence. Nat Neurosci. 2014; 17: pp. 1658-1660.

Marshall L, Helgadóttir H, Mölle M, Born J. Boosting slow oscillations during sleep potentiates memory. Nature. 2006;444: pp. 610-613.

Javadi AH, Walsh V. Transcranial direct current stimulation (tDCS) of the left dorsolateral prefrontal cortex modulates declarative memory. Brain Stimulat. 2012;5: pp. 231-241.

Rasch B, Büchel C, Gais S, Born J. Odor cues during slow-wave sleep prompt declarative memory consolidation. Science 2007;315: pp. 1426-1429.

Rudoy JD, Voss JL, Westerberg CE, Paller KA. Strengthening Individual Memories by Reactivating Them During Sleep Science. 2009;326: p. 1079.

Bendor D, Wilson MA. Biasing the content of hippocampal replay during sleep. Nat. Neurosci. 2012;15: pp. 1439-1444.

Abeyratne UR, Swarnkar V, Rathnayake SI, Hukins C. Sleep-stage and event dependency of brain asynchrony as manifested through surface EEG. Conf. Proc. Annu. Int. Conf. IEEE Eng. Med. Biol. Soc. IEEE Eng. Med. Biol. Soc. Conf. 2007;2007: pp. 709-712.

Salmi T, Brander PE. Computer assisted detection of REM and non-REM sleep for analysis of nocturnal hypoxaemia in patients with ventilatory impairment. Int. J. Clin. Monit. Comput. 1994;11: pp. 63-70.

Euston et al. Fast-Forward Playback of Recent Memory Sequences in Prefrontal Cortex During Sleep. Science. Nov. 2007; 318 (5853): pp. 1147-1150.

The SenseWear armband as a Sleep Detection Device [Internet], [cited Nov. 23, 2014]. pp. 1-9. Available from: http://www.bodymedia.com/Professionals/Whitepapers/The-SenseWear-armband-as-a-Sleep-Detection-Device?whence=.

Ruffini et al., Optimization of multifocal transcranial current stimulation for weighted cortical pattern targeting from realistic modeling of electric fields, Neuroimage, 89:216-25, 2014.

Rissman and Wagner, "Distributed Representations in Memory: Insights from Functional Brain Imaging," Annual Rev Psychol, 63: 101-128, 2012.

Rolls, "The Mechanisms for Pattern Completion and Pattern Separation in the Hippocampus," Frontiers in Systems Neuroscience, 7: 74, 2013.

McHugh et al., "Dentate Gyrus NMDA Receptors Mediate Rapid Pattern Separation in the Hippocampal Network," Science, 317(5834): 94-99, 2007.

Michael Schirner, et al., "An automated pipeline for constructing personalized virtual brains from multimodal neuroimaging data," NeuroImage, vol. 117, Aug. 15, 2015, pp. 343-357.

Office Action 1 for U.S. Appl. No. 15/227,922, dated Dec. 13, 2016.

Tremblay, Sara, et al. "The Uncertain Outcome of Prefrontal TDCS." Brain Stimulation 7.6 (2014): 773-83. Web.

Segrace, R.A. et al. "Concurrent Cognitive Control Training Augments the Antidepressant Efficacy of TDCS: A Pilot Study." Brain Stimulation 7.2 (2014): 325-31. Web.

Castano-Candamil, Ssebastian et al. "Solving the EEG Inverse Problem Based on Space-Time-Frequency Structured Sparsity Constraints." Neuroimage 118 (2015) 598-612. Web.

Marshall, L. "Transcranial Direct Current Stimulation during Sleep Improves Declarative Memory." Journal of Neuroscience 24.44 (2004): 9985-992. Web.

Javadi, Amir Homayoun, and Paul Cheng. "Transcranial Direct Current Stimulation (tDCS) Enhances Reconsolidation of Long-Term Memory." Brain Stimulation 6.4 (2013): 668-74. Web.

Sahlem, Gregory L., et al. "Oscillating Square Wave Transcranial Direct Current Stimulation (tDCS) Delivered During Slow Wave Sleep Does Not Improve Declarative Memory More Than Sham: A Randomized Sham Controlled Crossover Study." Brain Stimulation 8.3 (2015): 528-34. Web.

Barham, Michael P., Peter G. Enticott, Russell Conduit, and Jarrad A.g. Lum. "Transcranial Electrical Stimulation during Sleep Enhances Declarative (but Not Procedural) Memory Consolidation: Evidence from a Meta-analysis." Neuroscience & Biobehavioral Reviews 63 (2016): 65-77. Web.

Eggert, Torsten, Hans Dorn, Cornelia Sauter, Michael A. Nitsche, Malek Bajbouj, and Heidi Danker-Hopfe. "No Effects of Slow Oscillatory Transcranial Direct Current Stimulation (tDCS) on Sleep-Dependent Memory Consolidation in Healthy Elderly Subjects." Brain Stimulation 6.6 (2013): 938-45. Web.

Westerberg, Carmen E., Susan M. Florczak, Sandra Weintraub, M.-Marsel Mesulam, Lisa Marshall, Phyllis C. Zee, and Ken A. Paller. "Memory Improvement via Slow-oscillatory Stimulation during Sleep in Older Adults." Neurobiology of Aging 36.9 (2015): 2577-586. Web.

Response to Office Action 1 for U.S. Appl. No. 15/227,922, dated Mar. 13, 2017.

Office Action 2 for U.S. Appl. No. 15/227,922, dated Apr. 24, 2017.

Response to Office Action 2 for U.S. Appl. No. 15/227,922, dated Aug. 24, 2017.

Office Action 3 for U.S. Appl. No. 15/227,922, dated Sep. 29, 2017.

Response to Office Action 3 for U.S. Appl. No. 15/227,922, dated Jan. 29, 2018.

Notice of Allowance for U.S. Appl. No. 15/227,922, dated May 30, 2018.

Notification of Transmittal of International Search Report and the Written Opinion of the International Searching Authority for PCT/US2019/025629; dated Jul. 15, 2019.

International Search Report of the International Searching Authority for PCT/US2019/025629; dated Jul. 15, 2019.

Written Opinion of the International Searching Authority for PCT/US2019/025629; dated Jul. 15, 2019.

Notification of Transmittal of International Search Report and the Written Opinion of the International Searching Authority for PCT/US2018/034761; dated Sep. 21, 2018.

International Search Report of the International Searching Authority for PCT/US2018/034761; dated Sep. 21, 2018.

Written Opinion of the International Searching Authority for PCT/US2018/034761; dated Sep. 21, 2018.

(56) References Cited

OTHER PUBLICATIONS

Nir Grossman, et al., (2017). Noninvasive Deep Brain Stimulation via Temporally Interfering Electric Fields Cell 169, pp. 1029-1041 Jun. 1, 2017. Elsevier Inc. http://dx.doi.org/10.1016/j.cell.2017.05.024.
Woods et al. (2016). A technical guide to tDCS, and related non-invasive brain stimulation tools. Clinical Neurophysiology, 127: pp. 1031-1048.
Santostasi, Giovanni, et al. "Phase-locked loop for precisely timed acoustic stimulation during sleep." Journal of neuroscience methods 259 (2016): pp. 101-114.
Liu, Hechen, and Markus Schneider. "Similarity measurement of moving object trajectories." Proceedings of the third ACM SIGSPATIAL international workshop on geostreaming. ACM, 2012, pp. 19-22.
Communication pursuant to Rules 70(2) and 70a(2) EPC for the application for European Regional Phase Patent Application No. 18814040.4 , dated Mar. 10, 2021.
Rembado Irene, et al., "Cycle-Triggered Cortical Stimulation during Slow Wave Sleep Facilitates Learning a BMI Task: A Case Report in a Non-Human Primate," Frontiers in Behavioral Neuroscience, vol. 11, Jan. 1, 2017 (Jan. 1, 2017), pp. 59-59.
Notification of the International Preliminary Report on Patentability Chapter I for PCT/US2018/026614; dated Nov. 14, 2019.
The International Preliminary Report on Patentability Chapter I for PCT/US2018/026614; dated Nov. 14, 2019.
Communication pursuant to Rules 70(2) and 70a(2) EPC for the application for European Regional Phase Patent Application No. 18794804.7, dated Feb. 16, 2021.
Office Action 1 for U.S. Appl. No. 16/100,184, dated May 8, 2020.
Response to Office Action 1 for U.S. Appl. No. 16/100,184, dated Aug. 5, 2020.
Notice of Allowance for U.S. Appl. No. 16/100,184, dated Oct. 7, 2020.
Office Action 1 for U.S. Appl. No. 15/990,460, dated Aug. 5, 2019.
Response to Office Action 1 for U.S. Appl. No. 15/990,460, dated Nov. 5, 2019.
Notice of Allowance for U.S. Appl. No. 15/990,460, dated Nov. 15, 2019.
Notification of the International Preliminary Report on Patentability Chapter I for PCT/US2018/034761; dated Dec. 19, 2019.
The International Preliminary Report on Patentability Chapter I for PCT/US2018/034761; dated Dec. 19, 2019.
Office Action 1 for Chinese Patent Application No. 201880016061.3, dated Jul. 20, 2021.
English translation of Office Action 1 for Chinese Patent Application No. 201880016061.3, dated Jul. 20, 2021.
Machine English translation for Chinese patent application CN106512206 with publication date of Mar. 22, 2017.

\* cited by examiner

FIG. 6 ial Application No. 62/245,730, filed in the United States on Oct. 23, 2015, entitled, "Method and System to Accelerate Consolidation of Specific Memories Using Transcranial Stimulation," the entirety of which are hereby incorporated by reference.

This is a Continuation-in-Part Application of U.S. application Ser. No. 15/990,460, filed in the United States on May 25, 2018, entitled, "Targeted Steerable Transcranial Intervention to Accelerate Memory Consolidation," which is a Continuation-in-Part Application of U.S. application Ser. No. 15/332,787, filed in the United States on Oct. 24, 2016, which is a Non-Provisional patent application of U.S. Provisional Application No. 62/245,730, filed in the United States on Oct. 23, 2015, the entirety of which are hereby incorporated by reference. U.S. application Ser. No. 15/990, 460 is also a Continuation-in-Part Application of U.S. application Ser. No. 15/227,922, filed in the United States on Aug. 3, 2016, issued as U.S. Pat. No. 10,092,753 on Oct. 9, 2018, which is a Non-Provisional patent application of U.S. Provisional Application No. 62/210,907, filed in the United States on Aug. 27, 2015, entitled, "Method to Enhance Specific Memories with tCS During Slow-Wave Sleep," U. S Provisional Application No. 62/210,890, filed in the United States on Aug. 27, 2015, entitled, "Transcranial Intervention to Weaken Traumatic Memories," and U.S. Provisional Application No. 62/247,435, filed in the United States on Oct. 28, 2015, entitled, "Mapping Transcranial Signals to Transcranial Stimulation Required to Reproduce a Brain State," the entirety of which are hereby incorporated by reference. U.S. application Ser. No. 15/990,460 is also a Continuation-in-Part Application of U.S. application Ser. No. 15/947,733, filed in the United States on Apr. 6, 2018, which is a Non-Provisional patent application of U.S. Provisional Application No. 62/516,350, filed in the United States on Jun. 7, 2017, the entirety of which are hereby incorporated by reference. U.S. application Ser. No. 15/947, 733 is a Continuation-in-Part Application of U.S. application Ser. No. 15/332,787, filed in the United States on Oct. 24, 2016, entitled, "Method and System to Accelerate Consolidation of Specific Memories Using Transcranial Stimulation," which is a Non-Provisional patent application of U.S. Provisional Application No. 62/245,730, filed in the United States on Oct. 23, 2015, entitled, "Method and System to Accelerate Consolidation of Specific Memories Using Transcranial Stimulation," the entirety of which are hereby incorporated by reference. U.S. application Ser. No. 15/947,733 is a Continuation-in-Part Application of U.S. application Ser. No. 15/583,983, filed in the United States on May 1, 2017, entitled, "System and Method for Neurostimulation-Enhanced Second Language Acquisition," which is a Non-Provisional patent application of U.S. Provisional Application No. 62/330,440, filed in the United States on May 2, 2016, entitled, "A Method for Neurostimulation-Enhanced Second Language Acquisition," the entirety of which are hereby incorporated by reference. U.S. application Ser. No. 15/990,460 is also a Non-Provisional patent application of U.S. Provisional Application No. 62/570,669, filed in the United States on Oct. 11, 2017, U.S. Provisional Application No. 62/558,133, filed in the United States on Sep. 13, 2017, and U.S. Provisional Application No. 62/537, 892, filed in the United States on Jul. 27, 2017, the entirety of which are hereby incorporated by reference.

This is ALSO a Non-Provisional Application of U.S. Provisional Application No. 62/681,503, filed in the United States on Jun. 6, 2018, entitled, "System and Method to Cue Specific Memory Recalls While Awake," the entirety of which is incorporated herein by reference.

GOVERNMENT LICENSE RIGHTS

This invention was made with government support under U.S. Government Contract Number DARPA BTO W911NF-16-C-0018. The government has certain rights in the invention.

BACKGROUND OF INVENTION

(1) Field of Invention

The present invention relates to a system for cueing recall of specific memories, and more particularly, to a system for cueing recall of specific memories by associating a stimulation pattern with a memory during a waking experience and, subsequently, promoting recall of the memory during wake by applying the same stimulation pattern.

(2) Description of Related Art

In operational tasks, such as business and educational scenarios, it can be critically important to quickly integrate and accurately recall memories based on limited exposure to information. One simple way to prompt recall of a specific memory is to have a person or an automated system send a reminder (e.g., a calendar reminder). The reminder must describe the memory in enough detail to prompt the memory recall. However, in cases where a memory is subtle and less easily described, such a reminder may not be practical. For example, a procedural skill, such as how to perform a tennis serve, is a coordinated orchestration of movements, and a student practices with a teacher. At some point, the teacher can announce that the student has properly executed a serve, but that serve must be practiced many times to "internalize" it. For such a memory, simple descriptors are too indirect; they cannot capture the complex feeling of such a complex task, such as performing the serve.

In state-of-the-art laboratory experiments, auditory or olfactory cues are associated with simplistic laboratory tasks during performance, such as remembering the location of an icon on a two-dimensional (2D) grid, and these cues are then used during sleep to trigger replays of that task performance memory, thereby consolidating the memory during sleep. This has been shown to result in improved behavioral performance during the next waking period (see the List of Incorporated Literature References, see Literature Reference Nos. 1, 2, and 3). However, these cues have not been used to trigger memory recall during the waking period, and in any case, are impractical for operational use during waking periods because they can be lost in the complex ambient environment, and there are limited numbers of such cues that are uniquely discriminable. Additionally, drugs are also used in the prior art to improve memory in general (see Literature Reference Nos. 4 and 5), but they cannot selectively enhance a particular memory.

Thus, a continuing need exists for a system for memory reactivation that can be used to cue recall of a specific memory when needed while awake.

SUMMARY OF INVENTION

The present invention relates to a system for cueing recall of specific memories, and more particularly, to a system for cueing recall of specific memories by associating a stimulation pattern with a memory during a waking experience and, subsequently, promoting recall of the memory during wake by applying the same stimulation pattern. The system comprises one or more processors and a non-transitory computer-readable medium having executable instructions encoded thereon such that when executed, the one or more processors perform multiple operations. The system sends an initiation signal to a memory recall controller to select a stored stimulation pattern previously associated with a specific memory of an event. The memory recall controller is caused to initiate delivery of the selected stimulation pattern to a brain in a waking state for a duration of the event via a brain stimulation system. Following completion of the event, the system signals the memory recall controller to stop the brain stimulation system from delivering the selected stimulation pattern.

In another aspect, the initiation signal is generated by one of a user and an external automated system.

In another aspect, the stored stimulation pattern comprises at least one event descriptor corresponding to a salient feature of the event, and the external automated system tracks salient features of the user's environment and actions such that when the salient features match the at least one event descriptor, the external automated system generates the initiation signal.

In another aspect, the system generates the stored stimulation pattern as follows. When a user is going to experience a new event for recall at a later time, the system sends an initiation signal to the memory recall controller to select a unique stimulation pattern. The memory recall controller is caused to initiate delivery of the unique stimulation pattern to the brain for a duration of the new event via the brain stimulation system. Following completion of the new event, the system signals the memory recall controller to stop the brain stimulation system from delivering the unique stimulation pattern. The unique stimulation pattern is stored with at least one event descriptor of the new event.

In another aspect, the system provides instructions to a user to relax prior to causing the memory recall controller to initiate delivery of the selected stimulation pattern.

In another aspect, the system is configured for receiving feedback from a user that is ready to receive delivery of the selected stimulation pattern.

In another aspect, the brain stimulation system comprises a neural cap having one or more electrodes.

In another aspect, delivery of the selected stimulation pattern is initiated based on a change in location detected via global positioning system (GPS) coordinates.

In another aspect, the new event is a recognized driving situation, and delivery of the unique stimulation pattern prompts recall of an appropriate skill to deal with the recognized driving situation.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a system for cueing recall of specific memories, and more particularly, to a system for cueing recall of specific memories by associating a stimulation pattern with a memory during a waking experience and, subsequently, promoting recall of the memory during wake by applying the same stimulation pattern. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) List of Incorporated Literature References

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number, as follows:

1. Rudoy J D, Voss J L, Westerberg C E, Paller K A. Strengthening Individual Memories by Reactivating Them During Sleep. Science. 2009 Nov. 20; 326 (5956): 1079-1079.
2. Diekelmann S, Biggel S, Rasch B, Born J. Offline consolidation of memory varies with time in slow wave sleep and can be accelerated by cuing memory reactivations. Neurobiol Learn Mem. 2012 September; 98(2):103-11.
3. Rasch B, Buchel C, Gais S, Born J. Odor cues during slow-wave sleep prompt declarative memory consolidation. Science. 2007; 315(5817):1426-9.
4. Rasch B H, Born J, Gais S. Combined blockade of cholinergic receptors shifts the brain from stimulus encoding to memory consolidation. J Cogn Neurosci. 2006 May; 18(5):793-802.
5. Gais S, Born J. Low acetylcholine during slow-wave sleep is critical for declarative memory consolidation. Proc Natl Acad Sci USA. 2004 Feb. 17; 101(7):2140-4.

(2) Principal Aspects

Various embodiments of the invention include three "principal" aspects. The first is a system for cueing recall of specific memories during wake. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 1:
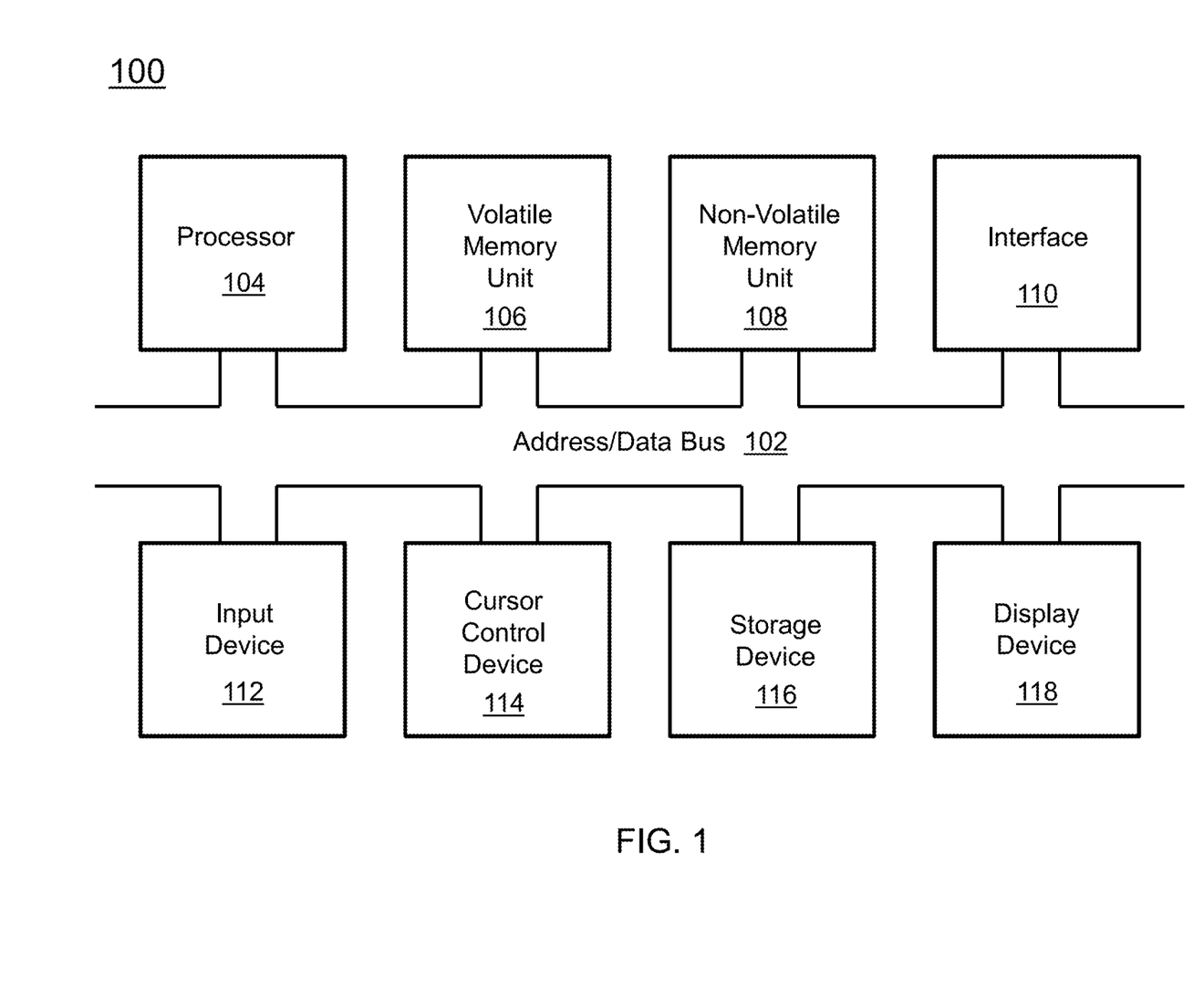
FIG. 1 is a block diagram depicting the components of a system for cueing specific memory recall according to some embodiments of the present disclosure.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. For instance, the system initiation signal 310 could be initiated by a wireless interface from a button in a convenient place on the body, like a smart watch. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
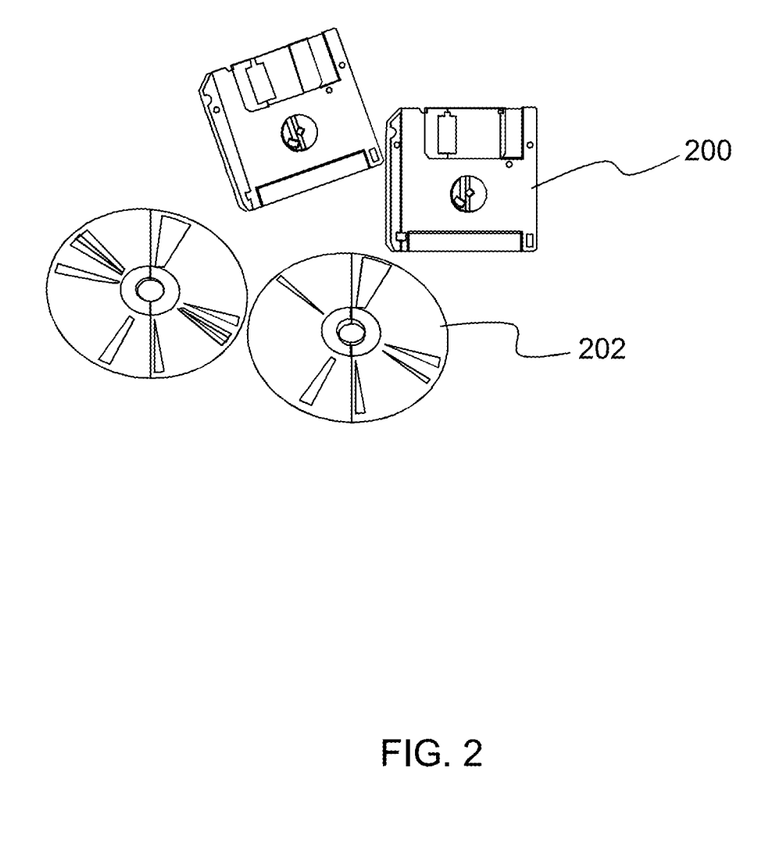
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the non-volatile memory of a computer or on a floppy disk, a CD-ROM, and a flash drive. In either event, the instructions are encoded on a non-transitory computer-readable medium.

(3) Specific Details of Various Embodiments

In operational tasks (as in many business and educational scenarios), it can be critically important to quickly integrate and accurately recall memories based on limited exposure to information. The invention described herein cues recall of a specific memory during waking. Once a memory is consolidated in long term memory, it is resistant to decay and can be recalled days, months, or years later. However, previously, there has been no way to cause the waking recall of one memory as opposed to another, whether consolidated or not. As described in detail below, the system according to embodiments of the present disclosure will cue the recall of a specific memory at some time after it is experienced, during waking, when it is needed. Specifically, the system applies a unique electrical or magnetic stimulation pattern to the brain during a waking state to cue recall of a memory that was previously associated with the same pattern. The number of unique patterns that can be generated are limited by the number of stimulation sites, so a large number of sites may be desirable (known as high-definition). Alternatively, U.S. Patent Publication No. 2018/0272129, which is hereby incorporated by reference as though fully set forth herein, taught a method that used interference patterns between a small number of electrodes to make the pattern move over time; such temporal movements can be used to generate a high definition pattern with a smaller number of electrodes.

The following is a description from U.S. application Ser. No. 15/332,787 (which is incorporated herein by reference), that describes memory consolidation and application of the stimulation. The memory to be consolidated is tagged by associating it with a cue. However, instead of audio or odor, the system applies a unique transcranial current stimulation (tCS) montage comprising a Spatio-Temporal Amplitude-Modulated Pattern (STAMP) of currents over sensory and association cortical sites during a distinct experience or skill learning. In general, STAMP can be any spatial, temporal, or spatiotemporal pattern of transcranial currents across the scalp over multiple channels (each applied to a different site on the scalp). The STAMP method according to embodiments of the present disclosure has the advantage that it will not degrade task performance or distract attention from learning the task. STAMP tagging does not need to compete with ambient noise or smells, and many more unique patterns are possible with STAMP. Additionally, transcranial current stimulation (tCS) may be applied to the prefrontal cortex (PFC) during specific encoding to strengthen memory formation and boost subsequent replay likelihood and fidelity.

STAMP is a weighted spatiotemporal function, and could be naturally instantiated using several endogenous brain rhythms (at theta, slow gamma, and fast gamma frequencies) that typically occur during attentive task performance across the brain, among others. tCS applies the STAMP across the scalp. Further, tDCS (DC transcranial stimulation) may be used on the PFC during the experience of the event to enhance the encoding strength as a means to enhance memory replay probability during subsequent offline periods. In addition, the approach according to various embodiments of the present disclosure is agnostic to stimulation technology and may be implemented through transcranial magnetic stimulation (TMS) as well. Further, electromagnetic STAMPs can be combined with unique sensory cues (e.g., audio or olfactory) to further achieve unprecedented levels of targeted memory tagging and cueing. Finally, the system can be implemented using current commercially available technologies (e.g., Neuroelectrics 32-channel tCS; EGI 128-channel tCS) and may be integrated into man-portable systems.

The STAMP tag is applied to the brain using electrical stimulation (e.g., tCS, tDCS) and is also stored (e.g., in a data storage drive). A STAMP stimulation montage can be created without reference to endogenous rhythms, simply as a unique set of DC or AC currents applied to the multiple electrodes across the scalp. The cumulative mean amplitude of the STAMP across the scalp, in one embodiment, will be about 2 milliamperes (mA). One skilled in the art could experiment with different values to find the optimal STAMP that is strong enough to "tag" the memory without overly influencing it. A STAMP tag can also be created in an analogous way using transcranial magnetic stimulation, or auditory or olfactory stimulation. These are alternative ways to associate a unique pattern with the memory to be recalled.

Figure 3:
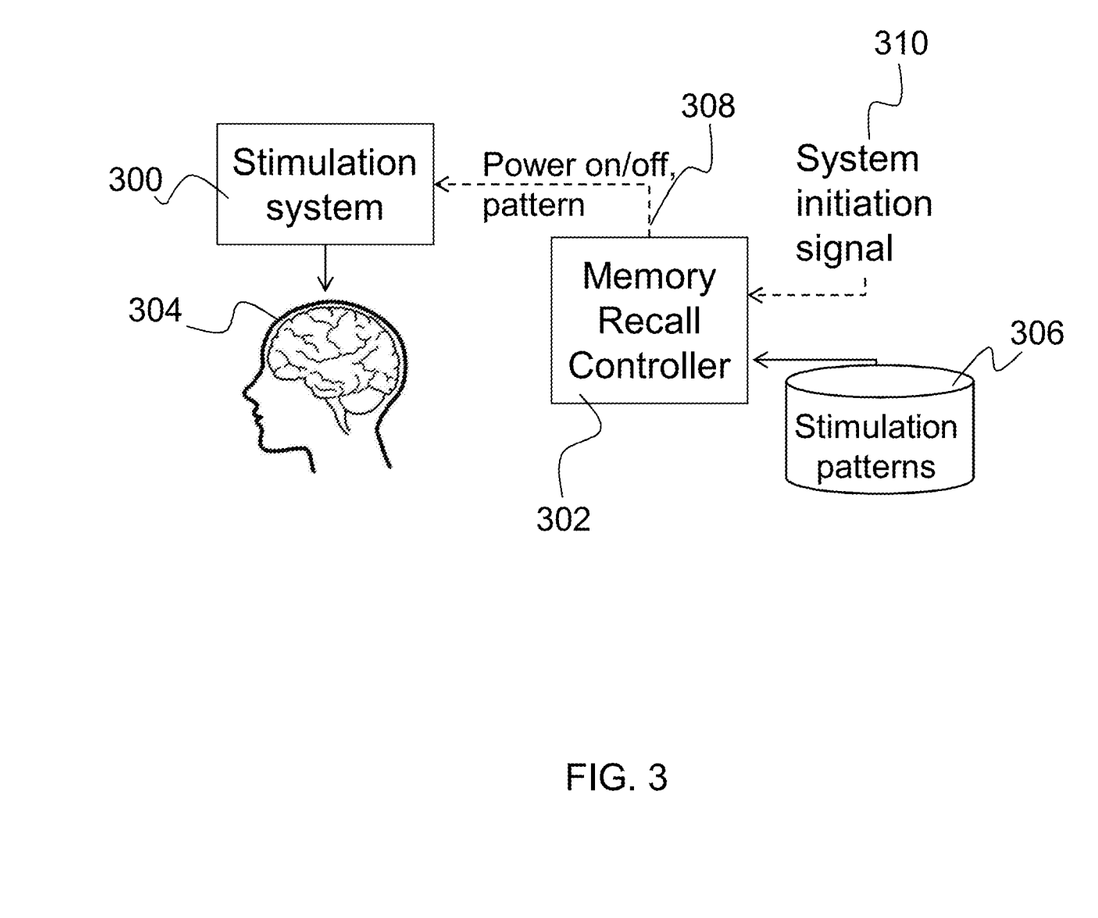
FIG. 3 is an illustration of a system flow for cueing specific memories while a user is awake according to some embodiments of the present disclosure.

FIG. 3 illustrates the system comprising a brain stimulation system 300 and a memory recall controller 302. As described above, a suitable brain stimulation system 300 is disclosed in U.S. application Ser. No. 15/332,787. In one embodiment, the brain stimulation system 300 is a high-definition, transcranial current stimulation (HD-tCS), which may be an AC (alternating current) or DC (direct current) system. A necessary property of the stimulation is that it be able to deliver a unique pattern to the brain 304. The higher the resolution of the stimulation, the more unique stimulation patterns 306 can be generated by a pattern generator, which is an a priori offline procedure that is not specific to any particular individual. Pattern generation is done iteratively. A set of maximally independent stimulation pattern vectors is generated specifying the level of stimulation to be applied to each place on the scalp, and ensuring the maximum current applied to any of the electrodes, as well as the total current across all electrodes, are within safe ranges.

A pattern generator can most simply be implemented by creating a normalized vector of random numbers, one for each stimulation electrode, and multiplying by the total amount of stimulation to be applied (2 mA is default). The result must be adjusted so that no electrode provides more than a safe amount of current (e.g., 1 mA default). It is most desirable if the pattern generated is maximally different from any other pattern that is created, so that each pattern cues a particular memory, and no other. One way to do this is by placing the set of generated vectors as columns in a matrix, A. Then, use Gaussian elimination to reduce the matrix to row-echelon form, B. The columns of B that contain leading 1's (the pivots) are the columns of A that form a maximal linearly independent set of vectors. Remove the other columns, and replace them with random vectors generated using the above procedure and repeat the Gaussian elimination method for linear independence, until all vectors are maximally independent. An example of a suitable pattern generator is also described in U.S. application Ser. No. 15/332,787.

When the memory is being encoded (that is, when the event is taking place and the user is experiencing the event, making a memory), the memory recall controller 302 turns on the application of stimulation (power on/off pattern 308) with a unique stimulation pattern. This stimulation pattern becomes associated with the memory because the cortical stimulation, like the sensory activity, is all connected to the cortical area that projects into the hippocampus, the seat of episodic memory in the brain. During subsequent waking experiences that may be hours, days, or possibly even months later, when the user needs help to recall that specific memory, a system initiation signal 310 induces the memory recall controller 302 to retrieve the same pattern associated with the memory when it was first encoded, and to apply it to the brain 304 again, cueing a recall of the memory.

In another aspect, the stimulation pattern consists of a transcranial electrical stimulation pattern to be applied to one or more electrodes applied to the scalp, or a transcranial magnetic stimulation (TMS) pattern or auditory or olfactory or other type, or a combination of those types. The additional signals may not be desirable or necessary, but if added, they could strengthen the cue associated with the memory depending upon the application. However, odor and audio are limited by human sensory acuity, which can vary widely between people, especially certain challenged populations such as seniors or those with cognitive deficits. Odors are also difficult to distinguish in certain environments such as those that are noisy, windy, or filled with smells, like some military operational environments. TMS and HD-tCS bypass the senses and directly stimulate the cortex.

In experimental studies on well over 100 human subjects, it was found that an HD-tCS stimulation pattern of 2 mA spread over 64 or 128 electrodes (where no electrode delivers more than 1 mA) is well tolerated and can appropriately tag a memory for later recall. These studies also used the STAMP stimulation patterns to associate with a memory during encoding, but was different than the invention described herein in that the memory was cued during sleep for the purpose of enhancing memory consolidation, and the behavioral recall test was performed during a subsequent daytime period without stimulation. The present invention does not operate at all during sleep, and only indirectly enhances memory consolidation as described above, and does reapply the stimulation pattern during a subsequent waking period to cue the memory. Also, unlike the prior art, the invention described herein is applied open loop, with no need for application at specific frequencies or stages of consciousness. The experimental studies did confirm the safety of the STAMP protocol and its ability to affect memory. A database of stimulation patterns 306 designed to be maximally unique is prepared beforehand, and patterns can be selected from that database by the memory recall controller 302. The database includes a list of unique patterns that were previously generated and stored and have not yet been associated with a memory.

Once a set of patterns is available, one can be selected at random when needed to "tag" a memory. When a pattern is selected, it is removed from the pool of available patterns, and stored along with a description of the memory it is associated with (in the encoding process). The description could take the form of a set of semantic tags that describe the memory, like "tennis-serve" or "parallel-parking". In practice, the semantic tag would best be supplied with reference to an ontology that identifies a context, like "vehicle-operation"/"automobile"/"parking"/"parallel". Such a semantic tagging scheme may be universal, and the same stimulation pattern could be used on different subjects. However, for a single individual, each stimulation pattern must be unique.

Figure 4:
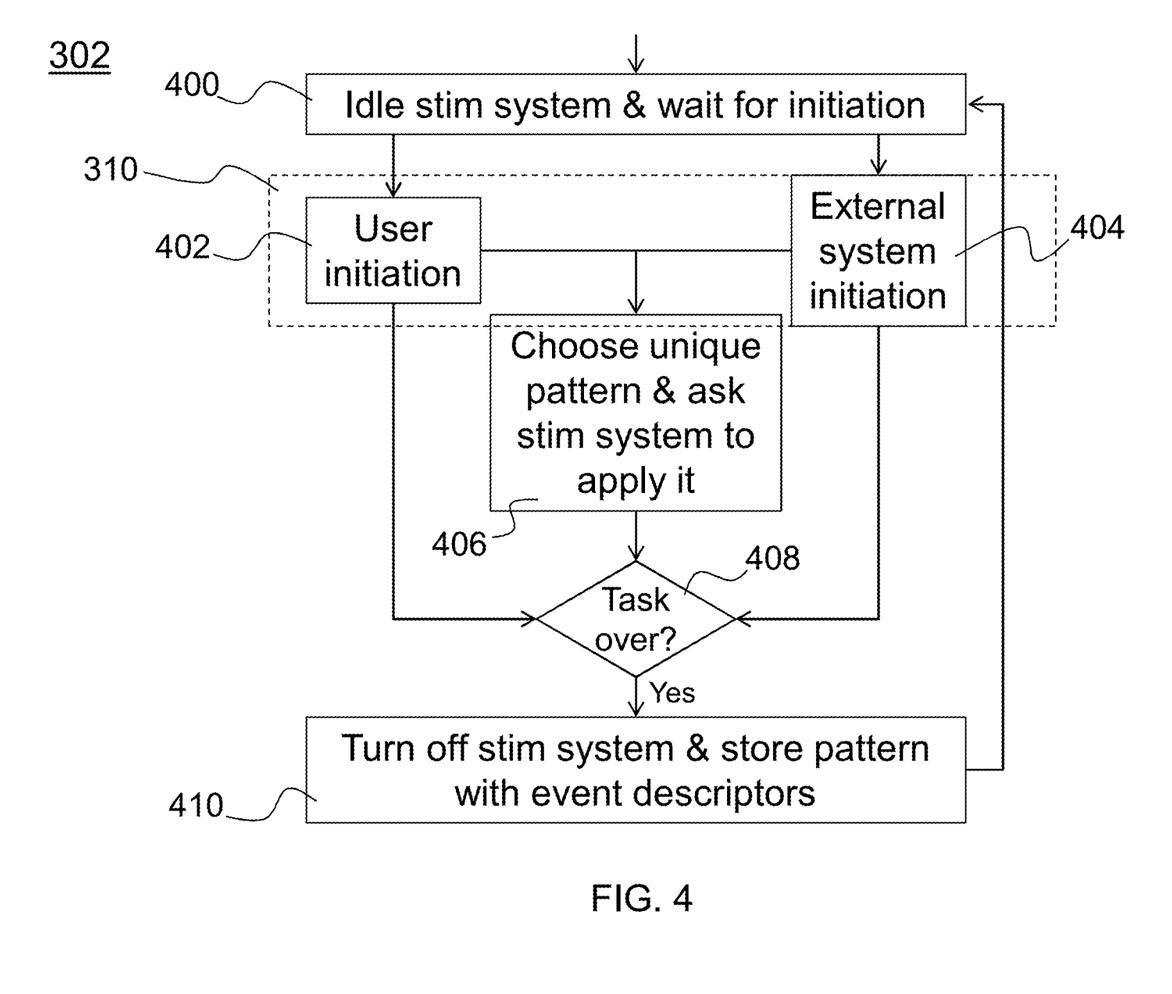
FIG. 4 is an illustration of memory recall controller flow during training according to some embodiments of the present disclosure.

FIG. 4 is a flow diagram depicting memory recall controller 302 flow during training (i.e., during memory encoding). When not operating, the stimulation system 300 is idle (400) and waiting for a power on, which would be applied in response to an initiation signal. The system initiation signal 310 can be either a user initiation signal 402 or an external system initiation signal 404, such as a change in location detected via GPS coordinates. Upon initiation, when the user is going to experience a new important event, the memory recall controller 302 chooses a unique stimulation pattern and induces the stimulation system 300 to apply 406 the unique stimulation pattern. The particular stimulation system may have proprietary ways to command it, but every system should have a roughly equivalent way of specifying a stimulation command to apply a vector of stimulation intensities to a set of electrodes and stop the stimulation on command. A non-limiting example of an important event that is to be remembered is a sequence of steps, such as how to perform cardiopulmonary resuscitation (CPR), a complicated and critical step in a mission rehearsal for a military raid, a tennis serve, some phase of vehicle operation, or a step in a factory manufacturing task. When the training event starts, the memory recall controller 302 turns on the stimulation system 300 to apply the chosen unique pattern (element 406). As described above, this can be initiated by the user (element 402) or by an external training system (element 404). When the event/task is over 408, the memory recall controller 302 is similarly signaled to stop the intervention by turning off the stimulation system 300 and storing the pattern with characteristic features of the event (i.e., event descriptors) for later use (element 410).

Figure 5:
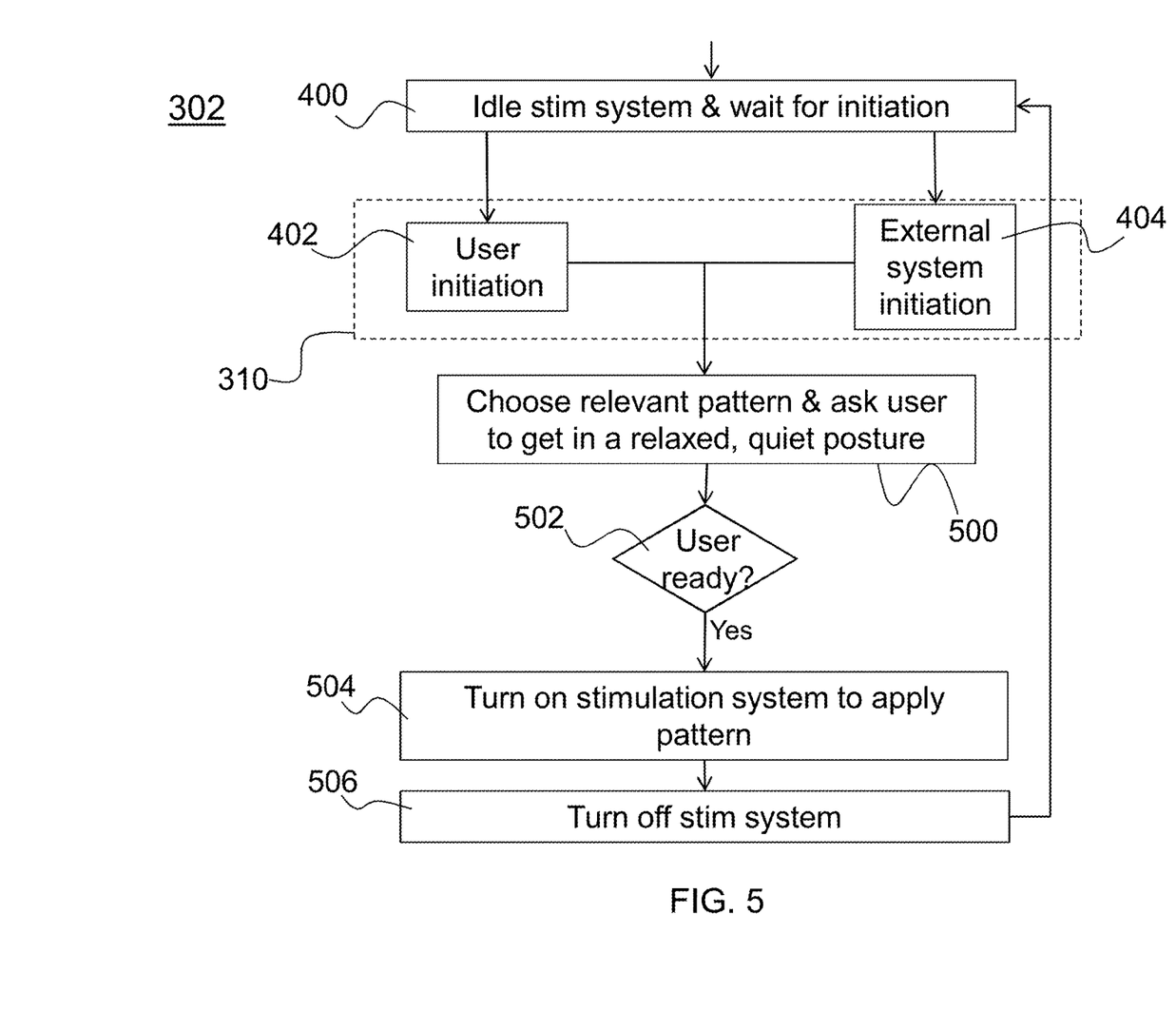
FIG. 5 is an illustration of memory recall controller flow during recall according to some embodiments of the present disclosure.

FIG. 5 depicts memory recall controller 302 flow during recall (i.e., when the user needs help in recalling the memory). At some later time, which may be hours, days, weeks, months, or even years later, when it is necessary for the specific memory to be recalled, either the user (element 402) or an external support system (element 404) can task the stimulation system 300 to apply the same pattern again (element 500), cueing recall of the memory. Memory recall will be most effective if the user is able to get into a relaxed quiet posture during the stimulation if possible, so the system will ask, request, or provide instructions for the user to do that. The system could do this with an audible request or, if a display screen is available to the user, an icon or textual request could be used. For the best results, the user could close eyes and count breaths for the duration of the recall stimulation. If the user is in the middle of some task, such as driving, that requires attention, they could pull over the car and park briefly while the intervention is applied. This is a safety consideration for cases where the memory recall procedure might be disorienting to the user. These are not necessary steps, but they can increase the efficacy of the intervention. When the user signals (i.e., provides feedback to the system) that they are ready to begin (element 502), the memory recall controller 302 turns on the stimulation of the pattern for a period of time (i.e., a duration of an event), which is typically approximately 10 seconds, but could be approximately 1 second, or approximately 100 seconds, or approximately 1000 seconds, for instance, to apply the pattern (element 504). The user can communicate this by clicking on the icon or textual alert provided by the system, or the system can communicated this to the user by commanding the user audibly through an audible command system. After the stimulation is applied, the stimulation system is idled (element 506).

Figure 6:
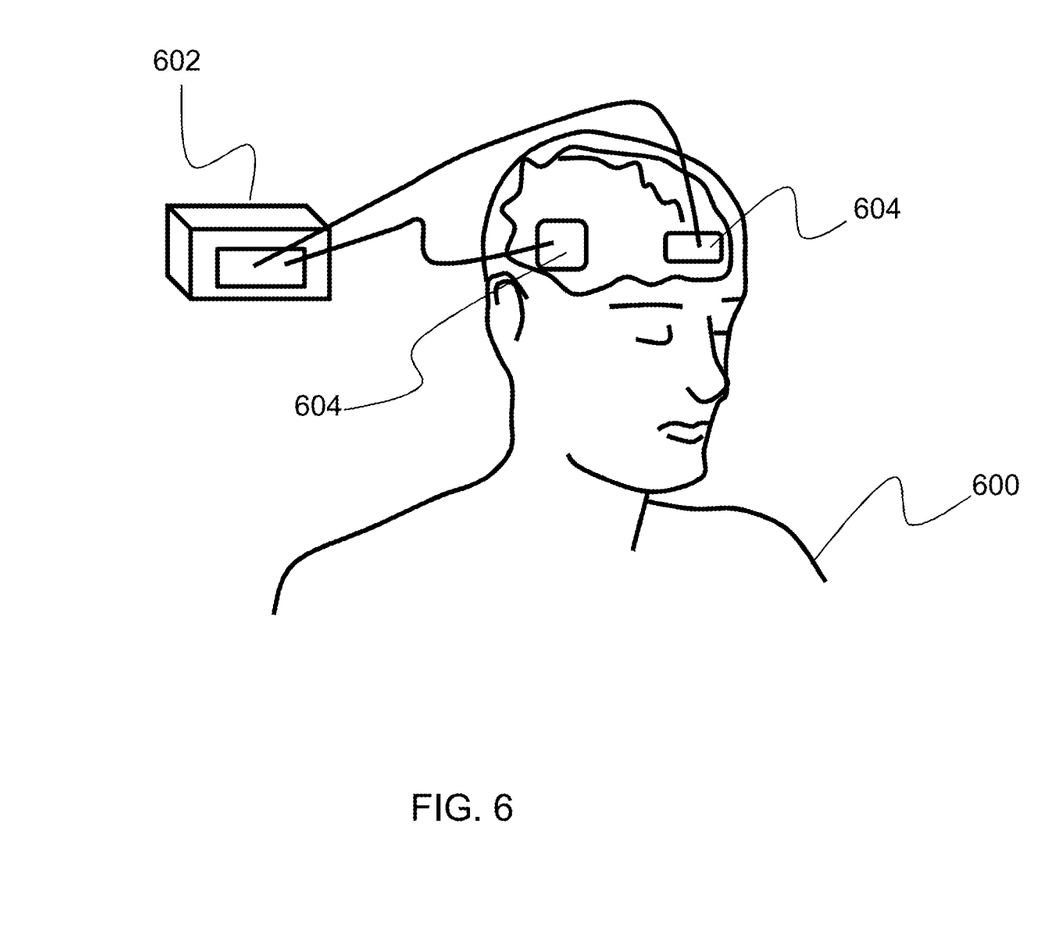
FIG. 6 is an illustration of a human subject receiving neurostimulation via a neural device according to some embodiments of the present disclosure.

FIG. 6 is an illustration of a human subject 600 receiving neurostimulation via a neural device 602. A neural device 602 able to generate an electrical current administers neurostimulation through neurostimulation components 604, such as HD-tCS stimulating electrodes, in direct physical contact with the human subject 600. The neurostimulation components 604 can be part of a neural cap wearable by the human subject 600. Current commercially available technologies (e.g., 32-channel HD-tCS by Neuroelectrics (located at 210 Broadway, Suite 201, Cambridge, Mass., 02139) can be plugged into wall-plug electricity, but some vendors are supplying man-portable units that can be run off a battery. There are also wireless connections to a stimulation cap, such as the Neuroelectrics Enobio32 system.

As described above, the memory recall controller 302 can initiate a stimulation event (elements 406 or 504) as a result of a signal from a user (element 402) or from an external automated system (element 404). One use case is a training system for military mission rehearsal. During training (depicted in FIG. 4) in a virtual or real mockup of the environment to be raided, the soldier might come to a particularly difficult or complex part of the mission, and turn on (element 402) the memory recall controller 302 to apply a unique pattern while that portion of the mission is being trained (element 406) or practiced (element 504. During the original training session, the system according to embodiments of the present disclosure may record the features of the environment (which could include accurate global positioning system (GPS) coordinates of the location), along with the unique stimulation pattern. The environmental features may be used as event descriptors to later access the appropriate pattern to be applied to recall the memory.

When the soldier is in the mission, an automated system (element 404), which is external to the system described herein, could track the soldier's progress and, when conditions (e.g., GPS coordinates, salient features from images of the soldier's surrounding, etc.) match the stored features of a location (e.g., GPS coordinates, features from images previously captured or from a model of the location, etc.), the system can automatically apply the stimulation pattern previously associated with the memory of what to do at that location (element 504). For example, upon detection of specific GPS coordinates, the external automated system (element 404) can apply the stimulation pattern to aid the soldier in recalling a previous scene and the locations of various elements in the scene, such as vehicles and buildings, and rooms, doors, and windows within a building, etc. The automated system (element 404) can include multiple sensors for providing data related to the user's movements and location, including, but not limited to, an accelerometer, a gyroscope, a magnetometer, GPS, and a proximity sensor.

An alternative use case could be entirely user initiated. For instance, if the new important event to be remembered is a sequence of steps like CPR, the user could initiate the training phase (element 402) as the CPR technique is being demonstrated (shown in FIG. 4). Then, sometime later, when CPR is required but the user has forgotten some of the details (shown in FIG. 5), the user could call up the pattern (element 402) in the pattern database using a keyword like "CPR", and the system would apply the stimulation and the memory would be recalled (element 504). In one embodiment, the user would need to be wearing the neural cap having electrodes and be, at least, wirelessly connected to a base station that would retrieve the stimulation pattern and control application of it. In another embodiment, the components/parts of the neural device 602 are miniaturized and made more ergonomic. For instance, stimulating electrodes could be integrated into a hat or tattooed onto a user's skull, and electronics integrated into a cell phone (or other mobile device) that is wirelessly connected to the electrodes, to control the stimulation.

As described above, U.S. application Ser. No. 15/332,787 described a way to associate such a pattern with a memory during waking experience, and then use that pattern during sleep to promote consolidation of the memory, requiring sensing of brain signals to identify particular sleeping brain states, and to apply stimulation using closed loop control at the frequency of the slow wave oscillation. The system according to embodiments of the present disclosure promotes recall of such a memory during wake, when it is needed, by applying a unique high-definition electrical or magnetic stimulation pattern to the brain during a quiet waking state to cue recall of a memory that was previously associated with the same pattern. The present disclosure employs open loop application of stimulation and there is no need to sense the EEG of the user during either training or subsequent use of the device. A waking memory reactivation technique is conceptually and operationally different than the aforementioned sleep consolidation methods; it is simpler since it can be operated in open-loop (i.e., there is no need to coordinate the application with a specific phase of a specific brain oscillation during a specific phase of sleep). It is applied only when needed for waking recall. Once a memory is consolidated in long term memory, it is resistant to decay and can be recalled days, months, or years later. The system will cue the recall of a specific memory at some time after it is consolidated, during waking, when it is needed.

If there are two similar memories, it is likely they will become merged when consolidated into long term memory and it will be difficult to extract one of the two. The system according to embodiments of the present disclosure can be used to cue the version that is most appropriate to the situation when it is needed based on features of the situation. For instance, salient features of the situation can be used to cue the correct version, such as parallel parking versus parking lot parking.

Additionally, seniors with normal types of memory performance reductions can get improvements in speed and accuracy of memory recall using the system described herein. It is possible that people with certain memory deficits, such as Alzheimer's, dementia, or even traumatic brain injury, could be assisted in recalling specific memories using the invention described herein.

Furthermore, an automated support system, such as a driver support system or a pilot associated system, can initiate the recall of an appropriate memory in a user if a situation warranted it by applying the appropriate stimulation pattern to the user. In semi-automated driving systems, or driver safety and support systems, the system according to embodiments of the present disclosure can be incorporated into a system to help a driver respond to recognized situations by prompting recall in the driver of the way to handle such a situation. In this example, a driver training program could associate a unique pattern of stimulation with each of a number of difficult situations, such as merging onto a freeway or turning left into a side street. When the driver encounters one of those situations, their semi-automated driving system would recognize the situation and apply the associated pattern to the driver, prompting recall of the appropriate skill to deal with the situation. Car navigation systems available on cell phones can recognize a left-hand turn, or a merge onto a freeway. In addition, pilot safety and support systems could make similar use of the invention as part of a pilot associated system.

Moreover, a soldier preparing for a mission could associate unique patterns with specific, intricate parts of the mission during training, and then, during the performance of the mission, self-initiate recalls to ensure clear and accurate performance. If the system is running on a cell phone, for instance, the user could initiate the system by saying "Recall X", or a similar audible command for recognition. "Recall" would be a command to start up the system described herein, and "X" would be a description for the system to locate the right stimulation pattern. Finally, the invention described herein is useful to anyone trying to remember specific details of a procedure, such as CPR. This is especially valuable if the procedure was learned a long time ago and the memory, although consolidated, has become "stale" because it has not been used.

Advantages of the system according to embodiments of the present disclosure might be explained by comparing it with the alternative of a person or a program reminding the user of a memory by describing some features of the memory. This may be impractical. A person who knows what memory is trying to be recalled may not be available, and an automated system may not be smart enough to know what features of the memory would be an appropriate cue. Even if such a reminder were available, the system described herein will cause recall of the actual memory which would be much more vivid than a suggestion of features of the memory. In other words, the electrical stimulation montage will prompt a clear recall of the original memory.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for cueing recall of a specific memory during wake, the system comprising:
   one or more processors and a non-transitory memory having instructions encoded thereon such that when the instructions are executed, the one or more processors perform operations of:
   when a user is going to experience a new event for recall at a later time, sending a first initiation signal;
   randomly selecting a unique stimulation pattern;
   initiating delivery of the unique stimulation pattern to a brain for a duration of the new event via a brain stimulation system, thus associating the unique stimulation pattern with a specific memory of the event;
   following completion of the new event, stopping the brain stimulation system from delivering the unique stimulation pattern; and
   storing the unique stimulation pattern with at least one event descriptor of the new event, and, for recall at the later time,
   upon receiving a second initiation signal, selecting the stored unique stimulation pattern previously associated with the specific memory of the event;
   initiating delivery of the stored unique stimulation pattern to the brain in a waking state for a duration of the event via the brain stimulation system; and
   following completion of the event, stopping the brain stimulation system from delivering the stored unique stimulation pattern.

2. The system as set forth in claim 1, wherein each of the first initiation signal and the second initiation signal is generated by one of a user and an external automated system.

3. The system as set forth in claim 2, wherein the stored unique stimulation pattern comprises at least one event descriptor corresponding to a salient feature of the event, and wherein the external automated system tracks salient features of the user's environment and actions such that when the salient features match the at least one event descriptor, the external automated system generates the second initiation signal.

4. The system as set forth in claim 1, wherein the one or more processors further perform an operation of providing instructions to a user to relax prior to initiating delivery of the unique stimulation pattern.

5. The system as set forth in claim 1, wherein the one or more processors are configured for receiving feedback from a user that is ready to receive delivery of the unique stimulation pattern.

6. A computer implemented method for cueing recall of a specific memory during wake, the method comprising an act of:
   causing one or more processors to execute instructions encoded on a non-transitory computer-readable medium, such that upon execution, the one or more processors perform operations of:
   when a user is going to experience a new event for recall at a later time, sending a first initiation signal;
   randomly selecting a unique stimulation pattern;
   initiating delivery of the unique stimulation pattern to a brain for a duration of the new event via a brain stimulation system, thus associating the unique stimulation pattern with a specific memory of the event;
   following completion of the new event, stopping the brain stimulation system from delivering the unique stimulation pattern; and
   storing the unique stimulation pattern with at least one event descriptor of the new event, and, for recall at the later time,
   upon receiving a second initiation signal, selecting the stored unique stimulation pattern previously associated with the specific memory of the event;
   initiating delivery of the stored unique stimulation pattern to the brain in a waking state for a duration of the event via the brain stimulation system; and
   following completion of the event, stopping the brain stimulation system from delivering the stored unique stimulation pattern.

7. The method as set forth in claim 6, wherein each of the first initiation signal and the second initiation signal is generated by one of a user and an external automated system.

8. The method as set forth in claim 7, wherein the stored unique stimulation pattern comprises at least one event descriptor corresponding to a salient feature of the event, and wherein the external automated system tracks salient features of the user's environment and actions such that when the salient features match the at least one event descriptor, the external automated system generates the second initiation signal.

9. The method as set forth in claim 6, wherein the one or more processors further perform an operation of providing instructions to a user to relax prior to initiating delivery of the unique stimulation pattern.

10. The method as set forth in claim 6, wherein the one or more processors are configured for receiving feedback from a user that is ready to receive delivery of the unique stimulation pattern.

11. A computer program product for cueing recall of a specific memory during wake, the computer program product comprising:
   computer-readable instructions stored on a non-transitory computer-readable medium that are executable by a computer having one or more processors for causing the processor to perform operations of:
   when a user is going to experience a new event for recall at a later time, sending a first initiation signal;
   randomly selecting a unique stimulation pattern;
   initiating delivery of the unique stimulation pattern to a brain for a duration of the new event via a brain stimulation system, thus associating the unique stimulation pattern with a specific memory of the event;
   following completion of the new event, stopping the brain stimulation system from delivering the unique stimulation pattern; and
   storing the unique stimulation pattern with at least one event descriptor of the new event, and, for recall at the later time,
   upon receiving a second initiation signal, selecting the stored unique stimulation pattern previously associated with the specific memory of the event;
   initiating delivery of the stored unique stimulation pattern to the brain in a waking state for a duration of the event via the brain stimulation system; and
   following completion of the event, stopping the brain stimulation system from delivering the stored unique stimulation pattern.

12. The computer program product as set forth in claim 11, wherein each of the first initiation signal and the second initiation signal is generated by one of a user and an external automated system.

13. The computer program product as set forth in claim 12, wherein the stored unique stimulation pattern comprises at least one event descriptor corresponding to a salient feature of the event, and wherein the external automated system tracks salient features of the user's environment and actions such that when the salient features match the at least one event descriptor, the external automated system generates the second initiation signal.

14. The computer program product as set forth in claim 11, wherein the one or more processors further perform an operation of providing instructions to a user to relax prior to initiating delivery of the unique stimulation pattern.

15. The computer program product as set forth in claim 11, wherein the one or more processors are configured for receiving feedback from a user that is ready to receive delivery of the unique stimulation pattern.

16. The system as set forth in claim 1, wherein the brain stimulation system comprises a neural cap having one or more electrodes.

17. The system as set forth in claim 1, wherein delivery of the stored unique stimulation pattern is initiated via the second initiation signal based on a change in location detected via global positioning system (GPS) coordinates.

18. The system as set forth in claim 1, wherein the new event is a recognized driving situation, and wherein delivery of the unique stimulation pattern prompts recall of an appropriate skill to deal with the recognized driving situation.

* * * * *